US012723070B2

(12) United States Patent
Lu et al.

(10) Patent No.: US 12,723,070 B2
(45) Date of Patent: Sep. 1, 2026

(54) ANTIBODY SPECIFICALLY BINDING TO STREP-TAG II TAG AND USE THEREOF

(71) Applicants: Imunopharm Technology Co., Ltd., Beijing (CN); BEIJING YIMIAOYILIAO CO., LTD, Beijing (CN)

(72) Inventors: Xinan Lu, Beijing (CN); Ting He, Beijing (CN); Feifei Qi, Beijing (CN); Ru Huang, Beijing (CN)

(73) Assignees: Imunopharm Technology Co., Ltd., Beijing (CN); BEIJING YIMIAOYILIAO CO., LTD, Beijing (CN)

( * ) Notice: Subject to any disclaimer, the term of this patent is extended or adjusted under 35 U.S.C. 154(b) by 638 days.

(21) Appl. No.: 18/256,599

(22) PCT Filed: Dec. 7, 2021

(86) PCT No.: PCT/CN2021/136113
§ 371 (c)(1),
(2) Date: Jun. 8, 2023

(87) PCT Pub. No.: WO2022/121899
PCT Pub. Date: Jun. 16, 2022

(65) Prior Publication Data

US 2024/0383970 A1 Nov. 21, 2024

(30) Foreign Application Priority Data

Dec. 8, 2020 (CN) ......................... 202011421882.0

(51) Int. Cl.

| | |
|---|---|
| ***C07K 16/1267*** | (2026.01) |
| ***C07K 1/22*** | (2006.01) |
| ***C07K 1/30*** | (2006.01) |
| ***G01N 33/58*** | (2006.01) |

(52) U.S. Cl.
CPC ............ *C07K 16/1292* (2013.01); *C07K 1/22* (2013.01); *C07K 1/30* (2013.01); *G01N 33/58* (2013.01); *C07K 2317/92* (2013.01); *C07K 2319/22* (2013.01)

(58) Field of Classification Search
None
See application file for complete search history.

(56) References Cited

FOREIGN PATENT DOCUMENTS

| | | | |
|---|---|---|---|
| CN | 111051349 | A | 4/2020 |
| CN | 111065409 | A | 4/2020 |
| CN | 112250767 | A | 1/2021 |
| EP | 2871189 | A1 | 5/2015 |
| WO | 2015067768 | A1 | 5/2015 |
| WO | 2019051128 | A1 | 3/2019 |
| WO | 2019051132 | A1 | 3/2019 |

OTHER PUBLICATIONS

International Search Report for International Application No. PCT/CN2021/136113, mailed Feb. 23, 2022.
Denham et al., "A generic cell surface ligand system for studying cell-cell recognition," Dec. 9, 2019, PLoS Biol, vol. 17(12), pp. 1-30.
Japanese Office Action for Application No. 2023-558928 dated Sep. 2, 2025 (5 pages total—English translation).
European Search Report and Written Opinion for application No. EP 21902604.4 dated Nov. 18, 2024.
Liu et al. "Inclusion of Strep-tag II in design of antigen receptors for T-cell immunotherapy" Feb. 22, 2016, Nature Biotechnology, 34(4):430-434.
Lulla et al. "A hidden gene in astroviruses encodes a viroporin" Aug. 13, 2020, Nature Communications, 11 (1):1-15.

*Primary Examiner* — Christina M Borgeest
(74) *Attorney, Agent, or Firm* — DLA Piper LLP (US)

(57) ABSTRACT

Disclosed is an antibody that specifically binds to a Strep-Tag II tag, and further disclosed are an amino acid sequence of the antibody of the present invention, a cloning or expression vector, a host cell, and a method for expressing or separating the antibody, and also disclosed is a composition comprising the antibody of the present invention. Also disclosed is a method for detecting or purifying a biological sample expressing the Strep-Tag II Tag by means of using the antibody of the present invention.

20 Claims, 2 Drawing Sheets

Specification includes a Sequence Listing.

ANTIBODY SPECIFICALLY BINDING TO STREP-TAG II TAG AND USE THEREOF

INCORPORATION BY REFERENCE OF SEQUENCE LISTING

The material in the accompanying sequence listing is hereby incorporated by reference into this application. The accompanying sequence listing txt file, named AJ7552PCT2101_REPLACEMENT_SEQUENCE_LISTING.txt, was created on Nov. 7, 2023 and is 21,373 bytes in size.

TECHNICAL FIELD

The present invention relates to an antibody that specifically binds to Strep-Tag II tag, and discloses the amino acid sequence of the antibody, a cloning or expression vector, a host cell, a method for producing the antibody, and a method of using the antibody to purify or detect biological sample expressing Strep-Tag II tag.

BACKGROUND ART

With the development of tumor immunotherapy, CAR-T (Chimeric antigen receptor-T cell) and TCR-T (T cell receptor-T cell, engineered T cell receptor T cell) and other immune cell therapies strategies have received great attention. The expansion level of CAR-T or TCR-T in vivo is an important indicator of its efficacy. Therefore, the development of reagents or methods for rapid and accurate detection of cells will help to effectively monitor the expansion efficiency thereof in vitro and in vivo.

There are currently two methods for detecting CAR-T or TCR-T cells: using quantitative real time PCR (qPCR) to detect the gene expression of CAR or TCR in T cells; and detecting the CAR protein or TCR protein expression in T cells. For the detection of CAR protein expression in T cells, T cells are detected by flow cytometry commonly with an antibody that specifically binds to scFv (Single-chain variable fragment) fragment in the CAR protein, or an antibody binding to Fab fragment, or a protein L and likewise. For the detection of TCR protein expression in T cells, a complex of HLA and peptides specifically targeting a particular TCR is commonly used for flow cytometry assays on T cells. However, above detection methods have obvious limitations. The qPCR detection of gene copy number cannot accurately reflect CAR-expressing T cells, because cells that integrate CAR genes may not normally express CAR protein, causing false positives in the qPCR detection method. For the detection method of CAR protein positive T cells, the detection background value of Fab antibodies is high, easily causing false positives; protein L is only suitable for the detection of CARs with k light chain in scFv. Moreover, for antibodies targeting scFv fragments in CAR protein, as well as for HLA and polypeptide complexes targeting TCR, it is needed to screen different antibodies or complexes regarding different CAR proteins or TCRs, and establish relevant detection methods, which are time-consuming, inefficient and costly. If an accurate, sensitive and universal antibody detection of CAR-T can be developed, it will greatly improve the detection efficiency of gene-transduced cell therapy drugs and reduce the detection cost.

SUMMARY OF THE INVENTION

The present invention discloses an isolated antibody that specifically binds to a Strep-Tag II tag, comprising: a heavy chain variable region (hereinafter abbreviated as VH) and a light chain variable region (hereinafter abbreviated as VL), wherein the VH comprises: a VH-CDR1 comprising the amino acid sequence of SEQ ID NO: 1, a VH-CDR2 comprising the amino acid sequence of SEQ ID NO: 2 and a VH-CDR3 comprising the amino acid sequence of SEQ ID NO: 3 or SEQ ID NO: 4; and the VL comprises: a VL-CDR1 comprising the amino acid sequence of SEQ ID NO: 5 or SEQ ID NO: 6, a VL-CDR2 comprising the amino acid sequence of SEQ ID NO: 7 or SEQ ID NO: 8 and a VL-CDR3 comprising the amino acid sequence of SEQ ID NO: 9 or SEQ ID NO: 10.

In some embodiments, the VH comprises: a VH-CDR1 consisting of the amino acid sequence as set forth in SEQ ID NO: 1, a VH-CDR2 consisting of the amino acid sequence as set forth in SEQ ID NO: 2 and a VH-CDR3 consisting of the amino acid sequence as set forth in SEQ ID NO: 3 or SEQ ID NO: 4; and the VL comprises: a VL-CDR1 consisting of the amino acid sequence as set forth in SEQ ID NO: 5 or SEQ ID NO: 6, a VL-CDR2 consisting of the amino acid sequence as set forth in SEQ ID NO: 7 or SEQ ID NO: 8 and a VL-CDR3 consisting of the amino acid sequence as set forth in SEQ ID NO: 9 or SEQ ID NO: 10.

In some embodiments, the VH comprises: a VH-CDR1 comprising the amino acid sequence of SEQ ID NO: 1, a VH-CDR2 comprising the amino acid sequence of SEQ ID NO: 2 and a VH-CDR3 comprising the amino acid sequence of SEQ ID NO: 3.

In some embodiments, the VH comprises: a VH-CDR1 comprising the amino acid sequence of SEQ ID NO: 1, a VH-CDR2 comprising the amino acid sequence of SEQ ID NO: 2 and a VH-CDR3 comprising the amino acid sequence of SEQ ID NO: 4.

In some embodiments, the VL comprises: a VL-CDR1 comprising the amino acid sequence of SEQ ID NO: 5, a VL-CDR2 comprising the amino acid sequence of SEQ ID NO: 7 and a VL-CDR3 comprising the amino acid sequence of SEQ ID NO: 9.

In some embodiments, the VL comprises: a VL-CDR1 comprising the amino acid sequence of SEQ ID NO: 6, a VL-CDR2 comprising the amino acid sequence of SEQ ID NO: 8 and a VL-CDR3 comprising the amino acid sequence of SEQ ID NO: 10.

In some embodiments, the antibody comprises a VH and a VL, wherein the VH comprises: a VH-CDR1 comprising the amino acid sequence of SEQ ID NO: 1, a VH-CDR2 comprising the amino acid sequence of SEQ ID NO: 2 and a VH-CDR3 comprising the amino acid sequence of SEQ ID NO: 3; and the VL comprises: a VL-CDR1 comprising the amino acid sequence of SEQ ID NO: 5, a VL-CDR2 comprising the amino acid sequence of SEQ ID NO: 7 and a VL-CDR3 comprising the amino acid sequence of SEQ ID NO: 9.

In some embodiments, the antibody comprises a VH and a VL, wherein the VH comprises: a VH-CDR1 comprising the amino acid sequence of SEQ ID NO: 1, a VH-CDR2 comprising the amino acid sequence of SEQ ID NO: 2 and a VH-CDR3 comprising the amino acid sequence of SEQ ID NO: 4; and the VL comprises: a VL-CDR1 comprising the amino acid sequence of SEQ ID NO: 6, a VL-CDR2 comprising the amino acid sequence of SEQ ID NO: 8 and a VL-CDR3 comprising the amino acid sequence of SEQ ID NO: 10.

In some embodiments, the antibody comprises a VH and a VL, the VH comprising: a VH-CDR1 consisting of the amino acid sequence as set forth in SEQ ID NO: 1, a VH-CDR2 consisting of the amino acid sequence as set forth in SEQ ID NO: 2 and a VH-CDR3 consisting of the amino acid sequence as set forth in SEQ ID NO: 3; and the VL comprises: a VL-CDR1 consisting of the amino acid sequence as set forth in SEQ ID NO: 5, a VL-CDR2 consisting of the amino acid sequence as set forth in SEQ ID NO: 7 and a VL-CDR3 consisting of the amino acid sequence as set forth in SEQ ID NO: 9; or the VH comprises: a VH-CDR1 consisting of the amino acid sequence as set forth in SEQ ID NO: 1, a VH-CDR2 consisting of the amino acid sequence as set forth in SEQ ID NO: 2 and a VH-CDR3 consisting of the amino acid sequence as set forth in SEQ ID NO: 4, and the VL comprises: a VL-CDR1 consisting of the amino acid sequence as set forth in SEQ ID NO: 6, a VL-CDR2 consisting of the amino acid sequence as set forth in SEQ ID NO: 8 and a VL-CDR3 consisting of the amino acid sequence as set forth in SEQ ID NO: 10.

In the present invention, each CDR in the VHs and the VLs is identified by the Kabat numbering system.

In some embodiments, the VH comprises, or consists essentially of, or consists of the amino acid sequence of SEQ ID NO: 23 or 24, or the VH comprises, or consists essentially of, or consists of the amino acid sequence having 85% or more, preferably 90% or more, more preferably 95% or more, or further preferably 99% or more identity to SEQ ID NO: 23 or 24.

In some embodiments, the VL comprises, or consists essentially of, or consists of the amino acid sequence of SEQ ID NO: 25 or 26, or the VL comprises, or consists essentially of, or consists of the amino acid sequence having 85% or more, preferably 90% or more, more preferably 95% or more, or even more preferably 99% or more identity to SEQ ID NO: 25 or 26.

In some embodiments, the VH or VL of the antibody further comprises one or more framework region(s) (hereinafter abbreviated as FWR).

In some embodiments, the VH comprises one, two, three or four FWRs, each FWR comprising an amino acid sequence selected from the group consisting of the sequences as set forth in SEQ ID NOs: 11, 12, 13, 14, 15 and 16, an amino acid sequences with at least 90%, preferably at least 95%, more preferably at least 99% identity thereto, the amino acid sequences having one or more amino acid substitution(s), insertion(s) or deletion(s) compared with the amino acid sequence of any one of SEQ ID NOs: 11, 12, 13, 14, 15 and 16. In some specific embodiments, the aforementioned VH comprises four FWRs, wherein FWR1 comprises the amino acid sequence as set forth in SEQ ID NO: 11, FWR2 comprises the amino acid sequence as set forth in SEQ ID NO: 12 or SEQ ID NO: 13, FWR3 comprises the amino acid sequence as set forth in SEQ ID NO: 14 or SEQ ID NO: 15, and FWR4 comprises the amino acid sequence as set forth in SEQ ID NO: 16.

In some embodiments, the VL comprises one, two, three or four FWRs, each FWR comprising an amino acid sequence selected from the group consisting of the sequences as set forth in SEQ ID NOs: 17, 18, 19, 20, 21 and 22, an amino acid sequences with at least 90%, at least 95%, at least 99% identity thereto, the amino acid sequences having one or more amino acid substitution(s), insertion(s) or deletion(s) compared with the amino acid sequence of any one of SEQ ID NOs: 17, 18, 19, 20, 21 and 22. In some specific embodiments, the aforementioned VL comprises four FWRs, wherein FWR1 comprises the amino acid sequence as set forth in SEQ ID NO: 17 or SEQ ID NO: 18, FWR2 comprises the amino acid sequence as set forth in SEQ ID NO: 19, FWR3 comprises the amino acid sequence as set forth in SEQ ID NO: 20 or SEQ ID NO: 21, and FWR4 comprises the amino acid sequence as set forth in SEQ ID NO: 22.

In some embodiments, the VH comprises, or consists essentially of, or consists of the amino acid sequence of SEQ ID NO: 23, and the VL comprises, or consists essentially of, or consists of the amino acid sequence of SEQ ID NO: 25.

In some embodiments, the VH comprises, or consists essentially of, or consists of the amino acid sequence of SEQ ID NO: 24, and the VL comprises, or consists essentially of, or consists of the amino acid sequence of SEQ ID NO: 26.

In some embodiments, the heavy chain of the antibody comprises, or consists essentially of, or consists of the amino acid sequence of SEQ ID NO: 27 or 29, or the heavy chain of the antibody comprises, or consists essentially of, or consists of an amino acid sequence with at least 85%, preferably at least 90%, more preferably at least 95% or further preferably at least 99% identity to SEQ ID NO: 27 or 29.

In some embodiments, the light chain of the antibody comprises, or consists essentially of, or consists of the amino acid sequence of SEQ ID NO: 28 or 30, or the light chain of the antibody comprises, or consists essentially of, or consists of an amino acid sequence with at least 85%, preferably at least 90%, more preferably at least 95% or further preferably at least 99% identity to SEQ ID NO: 28 or 30.

In some embodiments, the heavy chain of the antibody comprises, or consists essentially of, or consists of the amino acid sequence of SEQ ID NO: 27, and the light chain of the antibody comprises, or consists essentially of, or consists of the amino acid sequence of SEQ ID NO: 28.

In some embodiments, the heavy chain of the antibody comprises, or consists essentially of, or consists of the amino acid sequence of SEQ ID NO: 29, and the light chain of the antibody comprises, or consists essentially of, or consists of the amino acid sequence of SEQ ID NO: 30.

In some embodiments, the aforementioned antibodies further comprise at least one of a heavy chain constant region and a light chain constant region. The heavy chain constant region is selected from mouse IgG1, mouse IgG2a, mouse IgG2b or mouse IgG3, and the light chain constant region is selected from K chain or λ chain. Preferably, the heavy chain constant region is mouse IgG1, and the light chain constant region is the κ chain of a mouse antibody.

In some embodiments, the aforementioned antibody is a full-length antibody, Fab, Fab', F(ab')2, Fv, scFv, monoclonal antibody, bispecific antibody or multispecific antibody.

The sequences of the exemplary antibodies are as set forth in Table 1 and the Sequence Listing.

TABLE 1

Exemplary Antibody Amino Acid Sequences

| | Clone ID | SEQ ID NO | Amino Acid Sequences |
|---|---|---|---|
| 8A882 | Heavy Chain | 23 | EVQLQQSGPELVKPGASVKMSCKASGYTFTDY YMKWVKQSHGKSLEWIGDINPNNGDTFYNQKF |

TABLE 1-continued

Exemplary Antibody Amino Acid Sequences

| Clone ID | | SEQ ID NO | Amino Acid Sequences |
|---|---|---|---|
| | Variable Region | | KGKATLTVDKSSSSAYMQLNSLTSEDSAVYYC<br>ARYYGNSSPWFAYWGQGTLVTVSA |
| | Heavy Chain | 27 | EVQLQQSGPELVKPGASVKMSCKASGYTFTDY<br>YMKWVKQSHGKSLEWIGDINPNNGDTFYNQKF<br>KGKATLTVDKSSSSAYMQLNSLTSEDSAVYYC<br>ARYYGNSSPWFAYWGQGTLVTVSAAKTTPPSV<br>YPLAPGSAAQTNSMVTLGCLVKGYFPEPVTVT<br>WNSGSLSSGVHTFPAVLQSDLYTLSSSVTVPS<br>SPRPSETVTCNVAHPASSTKVDKKIVPRDCGC<br>KPCICTVPEVSSVFIFPPKPKDVLTITLTPKV<br>TCVWDISKDDPEVQFSWFVDDVEVHTAQTQPR<br>EEQFNSTFRSVSELPIMHQDWLNGKEFKCRVN<br>SAAFPAPIEKTISKTKGRPKAPQVYTIPPPKE<br>QMAKDKVSLTCMITDFFPEDITVEWQWNGQPA<br>ENYKNTQPIMNTNGSYFVYSKLNVQKSNWEAG<br>NTFTCSVLHEGLHNHHTEKSLSHSPGK |
| | Light Chain Variable Region | 25 | SYMNWYQQKPGQPPKLLIYAASNLQSGIPARFS<br>GSGSGTDFTLNIHPVEEEDTATYYCQQITEDPW<br>TFGGRTKLEIK |
| | Light Chain | 28 | DIVLTQSPASLAVSLGQRATISCKASQSVDYDGD<br>SYMNWYQQKPGQPPKLLIYAASNLQSGIPARFSG<br>SGSGTDFTLNIHPVEEEDTATYYCQQITEDPWTF<br>GGRTKLEIKRADAAPTVSIFPPSSEQLTSGGASV<br>VCFLNNFYPKDINVKWKIDGSERQNGVLNSWTDQ<br>DSKDSTYSMSSTLTLTKDEYERHNSYTCEATHKT<br>STSPIVKSFNRNEC |
| 8F8D1 | Heavy Chain Variable Region | 24 | EVQLQQSGPELVKPGASVKMSCKASGYTFTDY<br>YMKWVKQSHGKRLEWIGDINPNNGDTFYNQKF<br>KGKATLTVDKSSSTAYMQLNSLTSEDSAVYYC<br>ARYYGRSSPWFPYWGQGTLVTVSA |
| | Heavy Chain | 29 | EVQLQQSGPELVKPGASVKMSCKASGYTFTDY<br>YMKWVKQSHGKRLEWIGDINPNNGDTFYNQKF<br>KGKATLTVDKSSSTAYMQLNSLTSEDSAVYYC<br>ARYYGRSSPWFPYWGQGTLVTVSAAKTTPPSV<br>YPLAPGSAAQTNSMVTLGCLVKGYFPEPVTVT<br>WNSGSLSSGVHTFPAVLQSDLYTLSSSVTVPS<br>SPRPSETVTCNVAHPASSTKVDKKIVPRDCGC<br>KPCICTVPEVSSVFIFPPKPKDVLTITLTPKV<br>TCVVVDISKDDPEVQFSWFVDDVEVHTAQTQP<br>REEQFNSTFRSVSELPIMHQDWLNGKEFKCRV<br>NSAAFPAPIEKTISKTKGRPKAPQVYTIPPPK<br>EQMAKDKVSLTCMITDFFPEDITVEWQWNGQP<br>AENYKNTQPIMNTNGSYFVYSKLNVQKSNWEA<br>GNTFTCSVLHEGLHNHHTEKSLSHSPGK |
| | Light Chain Variable Region | 26 | DIVLTQSPASLGVSLGQRATISCKASQSVDNSGD<br>SYMNWYQQKPGQPPKLLIYAASNLESGIPARFS<br>GSGSGTDFTLNIHPVEEEDAATYYCQQINEDPW<br>TFGGRTKLEIK |
| | Light Chain | 30 | DIVLTQSPASLGVSLGQRATISCKASQSVDNSGD<br>SYMNWYQQKPGQPPKLLIYAASNLESGIPARFS<br>GSGSGTDFTLNIHPVEEEDAATYYCQQINEDPW<br>TFGGRTKLEIKRADAAPTVSIFPPSSEQLTSGGA<br>SVVCFLNNFYPKDINVKWKIDGSERQNGVLNSW<br>TDQDSKDSTYSMSSTLTLTKDEYERHNSYTCEA<br>THKTSTSPIVKSFNRNEC |

The CDR sequences and FWR sequences of the exemplary antibodies are as set forth in Tables 2 and 3.

TABLE 2

CDR Sequences of Exemplary Antibodies

| Clone ID. | | SEQ ID NOs | Amino Acid Sequences |
|---|---|---|---|
| 8A882 | VH-CDR1 | 1 | GYTFTDYYMK |
| | VH-CDR2 | 2 | DINPNNGDTFYNQKFKG |
| | VH-CDR3 | 3 | YYGNSSPWFAY |

TABLE 2-continued

CDR Sequences of Exemplary Antibodies

| Clone ID. | | SEQ ID NOs | Amino Acid Sequences |
|---|---|---|---|
| | VL-CDR1 | 5 | KASQSVDYDGDSYMN |
| | VL-CDR2 | 7 | AASNLOS |
| | VL-CDR3 | 9 | QQITEDPWT |
| 8F8D1 | VH-CDR1 | 1 | GYTFTDYYMK |
| | VH-CDR2 | 2 | DINPNNGDTFYNQKFKG |

TABLE 2-continued

CDR Sequences of Exemplary Antibodies

| Clone ID. | | SEQ ID NOs | Amino Acid Sequences |
|---|---|---|---|
| | VH-CDR3 | 4 | YYGRSSPWFPY |
| | VL-CDR1 | 6 | KASQSVDNSGDSYMN |
| | VL-CDR2 | 8 | AASNLES |
| | VL-CDR3 | 10 | QQINEDPWT |

TABLE 3

FWR Sequences of Exemplary Antibodies

| Clone ID. | | SEQ ID NO | Amino Acid Sequences |
|---|---|---|---|
| 8A882 | VH-FWR1 | 11 | EVQLQQSGPELVKPGASVKMSCKAS |
| | VH-FWR2 | 12 | WVKQSHGKSLEWIG |
| | VH-FWR3 | 14 | KATLTVDKSSSSAYMQLNSLTSEDS AVYYCAR |
| | VH-FWR4 | 16 | WGQGTLVTVSA |
| | VL-FWR1 | 17 | DIVLTQSPASLAVSLGQRATISC |
| | VL-FWR2 | 19 | WYQQKPGQPPKLLIY |
| | VL-FWR3 | 20 | GIPARFSGSGSGTDFTLNIHPVEE EDTATYYC |
| | VL-FWR4 | 22 | FGGRTKLEIK |
| 8F8D1 | VH-FWR1 | 11 | EVQLQQSGPELVKPGASVKMSCKAS |
| | VH-FWR2 | 13 | WVKQSHGKRLEWIG |
| | VH-FWR3 | 15 | KATLTVDKSSSTAYMQLNSLTSEDS AVYYCAR |
| | VH-FWR4 | 16 | WGQGTLVTVSA |
| | VL-FWR1 | 18 | DIVLTQSPASLGVSLGQRATISC |
| | VL-FWR2 | 19 | WYQQKPGQPPKLLIY |
| | VL-FWR3 | 21 | GIPARFSGSGSGTDFTLNIHPVEE EDAATYYC |
| | VL-FWR4 | 22 | FGGRTKLEIK |

The present invention also discloses an isolated nucleic acid molecule encoding the aforementioned antibody.

The present invention also discloses a cloning vector or an expression vector, the expression vector comprises the aforementioned nucleic acid molecule.

The present invention also discloses a host cell comprising one or more of the aforementioned cloning vector or expression vector.

The present invention also discloses a method for producing the aforementioned antibody, comprising culturing the aforementioned host cell, and isolating the antibody.

The present invention also discloses a composition or kit, comprising the aforementioned antibody, and one or more pharmaceutically acceptable 15 excipient(s), diluent(s) or carrier(s).

The present invention also discloses a conjugate comprising the aforementioned antibody linked to a detectable label. Those skilled in the art will appreciate that any detectable label can be used to construct the conjugates of the present invention. Exemplary detectable labels include, but are not limited to, fluorescent labels, enzyme substrate labels, radioactive isotopes, digoxigenin, biotin or avidin, DNA molecules or gold for detection. Wherein the fluorescent labels include, but are not limited to, fluorescein, rhodamine, dansyl, phycoerythrin or Texas red. The enzyme substrate labels include, but are not limited to, horseradish peroxidase, alkaline phosphatase, glucoamylase, lysozyme, saccharide oxidase or β-D-galactosidase. The radioisotopes include, but are not limited to, $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, $^{32}P$, other lanthanides. The label may also be a luminescent label or a chromophore.

The present invention also discloses a composition or kit comprising the aforementioned conjugate and one or more pharmaceutically acceptable excipient(s), diluent(s) or carrier(s).

The present invention also discloses the use of the aforementioned antibody in preparation of a reagent or a kit for detecting a fusion polypeptide containing a Strep-Tag II tag in a sample.

The present invention also discloses a method for detecting a fusion polypeptide containing a Strep-Tag II tag in a sample, comprising (i) contacting the sample containing the fusion polypeptide with the isolated antibody of the present invention in vitro, under conditions that allow the interaction between the antibody and the fusion polypeptide, and (ii) detecting formation of complex between the antibody and the fusion polypeptide. Wherein the method of detecting the complex includes, but is not limited to at least one of flow cytometry, Western blot, immunohistochemistry, and immunofluorescence.

In some embodiments, the sample containing a Strep-Tag II tag is a CAR-T cell containing a Strep-Tag II tag.

The present invention also discloses a method for purifying a fusion polypeptide containing a Strep-Tag II tag in a sample, comprising (i) contacting the sample containing the fusion polypeptide in vitro with the isolated antibody of the present invention, under conditions that allow the interaction between the antibody and the fusion polypeptide, and (ii) purifying the complex formed between the antibody and the fusion polypeptide. Wherein the method of purifying includes, but is not limited to affinity chromatography, immunoprecipitation, and the like.

In some embodiments, the sample is a biological sample comprising at least one of blood, urine, saliva, lymph, cerebrospinal fluid, bone marrow, tissues and organs, cells.

In a specific embodiment, the blood comprises at least one of serum, plasma, and whole blood.

In some embodiments, the sample comprises chimeric antigen receptor cells or engineered cell receptor cells.

In some embodiments, the sample is a chimeric antigen receptor cell or an engineered cell receptor cell.

Beneficial Effects of Invention

The antibody of the present invention has stronger affinity, which can more specifically bind to a Strep-Tag II tag in chimeric antigen receptor cell or engineered cell receptor cell, and can effectively monitor amplification efficiency in vitro and in vivo of the chimeric antigen receptor cells or the engineered cell receptor cells.

DETAILED DESCRIPTION

Figure 1:
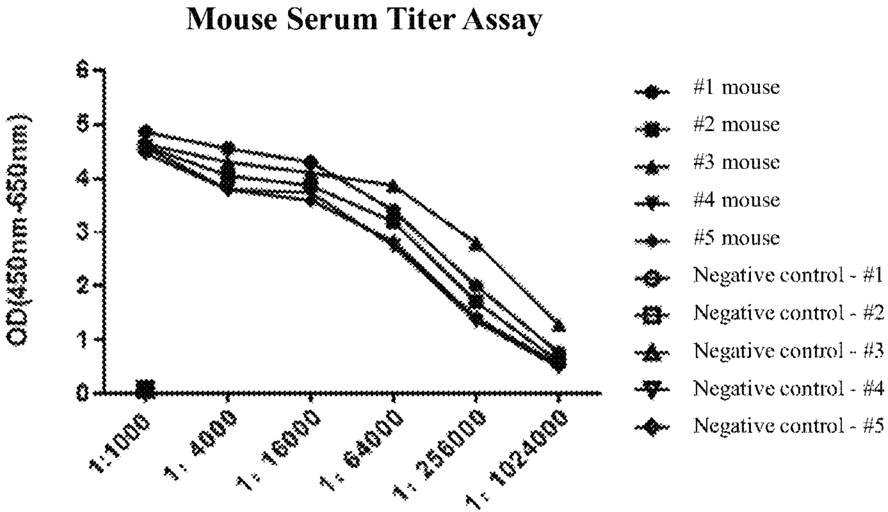
FIG. 1 shows the titer curve of serum from mice after four immunizations.

The present invention will be further described below through specific embodiments. Unless otherwise defined, terms used herein have the same meaning as commonly understood by those skilled in the art.

The term "antigen", as used herein, refers to a molecule that elicits an immune response, which may involve antibody production, or activation of specific immunocompetent cells. Those skilled in the art will understand that any macromolecule, including all proteins or peptides, can be used as an antigen. For example, the immunizing antigen in the present invention may be Strep-Tag II with the amino acid sequence for NWSHPQFEK, or may be Strep-Tag II conjugated to Keyhole Limpet Hemocyanin (KLH) (NWSHPQFEK-KLH). Antigens can be generated, synthesized, or can be derived from biological samples including, but not limited to, tissue samples, tumor samples, cells, or biological fluids. The term "detection antigen", as used herein, refers to an antigen used to determine antibody titer, such as Strep-Tag II conjugated to ovalbumin (OVA) (NWSHPQFEK-OVA), but those skilled in the art can understand the antigen is not limited to NWSHPQFEK-OVA, and antigens containing NWSHPQFEK or a part thereof can also be used as detection antigens, so the use of the specific detection antigen should not be considered as a limitation on the preparation method of the antibody.

The terms "peptide" and "polypeptide", as used herein, refer to compounds consisting of amino acid residues covalently linked by peptide bonds. As used herein, a "fusion polypeptide" refers to a polypeptide to which a Strep-Tag II tag is attached, such as a Strep-Tag II tag is attached to the N-terminal or C-terminal end of a heavy chain variable region or a light chain variable region in the extracellular domain scFv of a chimeric antigen receptor. Polypeptides comprise natural peptides, recombinant peptides, synthetic peptides, or combinations thereof.

The term "antibody", as used herein, is used in the broadest sense and encompasses a variety of antibody structures including, but not limited to, monoclonal antibodies, polyclonal antibodies, multispecific antibodies (eg, bispecific antibodies), full-length antibodies, and antibody fragments (or antigen-binding fragments, or antigen-binding portions), as long as they exhibit the desired antigen-binding activity. The antibodies comprise, but are not limited to, Fab, Fab', F(ab')2, Fv, scFv, di-scFv, tri-scFv, Fd, and other antibody fragments that retain antigen-binding function; it can also be a dimeric structure (Diabody) or a trimeric structure (Triabody). Antigen-binding fragments typically comprise an antibody light chain variable region (VL) and an antibody heavy chain variable region (VH), which can be further subdivided into hypervariable regions called complementarity determining regions (CDR), and more conserved regions called framework regions (FWR) that is interspersed. The CDRs of the antibodies and antigen-binding fragments disclosed in the present invention are defined or identified by Kabat numbering.

The full-length antibody refers to a protein comprising at least two heavy chains and two light chains interconnected by disulfide bonds. Each heavy chain consists of a heavy chain variable region and a heavy chain constant region, and each light chain consists of a light chain variable region and a light chain constant region. In a specific embodiment of the present invention, the heavy chain constant region can be selected from mouse-derived IgG1, IgG2a, IgG2b or IgG3, and the light chain constant region is selected from κ chain or λ chain.

The terms "chimeric antigen receptor" or "CAR", as used herein, refers to an artificial receptor engineered to be expressed on immune effector cells and capable of specifically binding an antigen. "Chimeric antigen receptor cells" refers to immune cells expressing artificial receptors that can specifically bind to antigens on cells, wherein immune cells comprise lymphocytes, natural killer cells, dendritic cells, monocytes/macrophages, granulocytes, mast cells, etc., and can be used for therapy using adoptive cell transfer. The term "engineered cell receptor" or "TCR", as used in the present invention, also known as engineered T cell receptor, is a heterodimer composed of peptide chains of TCR genetically engineered in vitro to enable more effective recognition of tumor intracellular antigenic peptides delivered by MHC, thereby killing and treating tumors. The fusion polypeptide in the present invention comprises CAR or TCR fused with Strep-Tag II tag.

As used herein, "isolated" means altered or removed from the natural state. For example, a nucleic acid or peptide naturally present in a living animal is not "isolated", but the same nucleic acid or peptide that is partially or completely separated from coexisting materials in its natural state is "isolated." An isolated nucleic acid or protein may be present in a substantially purified form, or may be present in a non-natural environment, such as a host cell. An "isolated" antibody is one that has been identified and separated from and/or recovered from components of its natural environment. In some embodiments, the antibody is purified to greater than 95% or 99% purity, as determined by electrophoresis (eg, SDS-PAGE, isoelectric focusing IEF, capillary electrophoresis) or chromatography (eg, ion exchange or reverse phase HPLC). As used herein, a host cell can be any prokaryotic or eukaryotic cell that contains a cloning vector or an expression vector, including those prokaryotic or eukaryotic cells that have been genetically engineered to contain a cloned gene in the chromosome or genome of the host cell. Special transgenic animals with modified immune systems can also be used to make antibodies.

The numerical limits or ranges stated herein are inclusive of the endpoints, and specifically include all values and subranges within the numerical limits or ranges.

The experimental methods in the following examples are conventional methods unless otherwise specified.

EXAMPLES

Example 1

Antigen, Mouse Immunization and Hybridoma Preparation

1. Antigen

Immunization antigen is a Strep-Tag II conjugated to Keyhole Limpet Hemocyanin (KLH) (NWSHPQFEK-KLH); detection antigen is a Strep-Tag II conjugated to ovalbumin (OVA) (NWSHPQFEK-OVA). All were purchased from Chinese Peptide Co., Ltd.

2. Immunization

Immunizing antigen protein (Strep-Tag II polypeptide conjugated to KLH (NWSHPQFEK-KLH)) was dissolved in physiological saline at a concentration of 0.5 mg/mL. 100 μL of the above-mentioned antigen protein solution was mixed with an equal volume of Freund's complete adjuvant (Sigma; Cat #: 1001646446) and immunized Balb/c mice (female, 6-8 weeks, purchased from Beijing Vital River Laboratory Animal Technology Co., Ltd.) by subcutaneous abdominal multipoint injection to produce an immune response. Then the above antigen protein solution was diluted with normal saline to a concentration of 0.25 mg/mL, and 100 μL of the diluted antigen protein solution and Fuchs' incomplete adjuvant (Sigma; Cat #: 1002036152) were mixed 1:1 by volume on days 15, 29 and 43, respectively, and immunized Balb/c mice by subcutaneous abdominal multipoint injection for booster immunization. Each mouse was injected with a volume of 200 μL per injection for a total of 4 antigen immunizations. Serum titers were determined by tail-docking blood on days 22, 36 and 50, respectively. Mouse serum titers were detected by enzyme-linked immunosorbent assay (ELISA) using NWSHPQFEK-OVA polypeptide, and the method was as follows: 1 μg/mL of OVA-conjugated Strep-Tag II (NWSHPQFEK-OVA) was added to 96-well plate at 4° C. (purchased from Corning) and left overnight, and the ELISA plates were washed and then washed times with phosphate buffered saline (PBST) containing 0.05% Tween-20. Plates were blocked with 1% bovine serum albumin for 2 hours at room temperature and washed 5 times with PBST. Then, the mouse serum was diluted 4 times from 1:1000 to 1:102400 and added to the ELISA plate, incubated at room temperature for 1 hour, and washed 5 times with PBST. 100 μL/well of HRP-labeled goat anti-mouse secondary antibody (Invitrogen, Cat #: 31430) was added, and incubated for 1 hour at room temperature after washing. 50 μL/well of 3,3',5,5'-tetramethylbenzidine (TMB) was then added to the plate, incubated at room temperature for 15 minutes, then the reaction was stopped and the results were read.

According to the detection results of the serum titers of the immunized mice, the titer results of 5 mice were shown (FIG. 1), and the titer of the No. #4 mouse was higher than that of other mice. Mouse #4 was selected for hybridoma fusion, and 3 days before fusion, mouse was injected intraperitoneally with 50 μg of immunizing antigen for shock.

3. Fusion

By polyethylene glycol fusion method, the spleen of mouse #4 was extracted, minced and resuspended with Dulbecco's Phosphate Buffered Saline (DPBS) to extract single cells of mouse spleen B cells, centrifuged at 500 g for 5 minutes, and the pellet was resuspended in DPBS, then the cells were washed by centrifugation at 500 g for 5 minutes, and the splenocytes were mixed with mouse myeloma cell line sp2/0 (purchased from Nordic Bioscience (Beijing) Co., Ltd.) in a ratio of 3:1 (the ratio of the number of cells), and 1 mL polyethylene glycol (Roche; Cat #: 10783641001) was added, the fused cells were resuspended in HAT medium (Gibco; Cat #: 21060-017), and plated on 96-well cell culture plates, after 7 days of culture at 37° C. in a carbon dioxide incubator, primary screening of hybridomas was performed by ELISA and flow cytometry. The selected hybridoma cells were cultured overnight at 37° C. in a carbon dioxide incubator, and then the fused cells were seeded into 96-well plates by limiting dilution.

Example 2

Screening of Positive Hybridoma Cells

The presence of anti-Strep-Tag II antibody in the culture supernatant of hybridoma was detected by ELISA test and flow cytometry, and the hybridoma cells that could proliferate indefinitely and secrete antibody were finally screened. Details as follows:

1. ELISA Screening

1 μg/mL OVA-conjugated Strep-Tag II (NWSHPQFEK-OVA) was added to a 96-well plate (purchased from Corning) overnight at 4° C., then the plate was washed 5 times with 0.05% Tween-20 in phosphate Buffer (PBST) after the supernatant was discarded. Plates were blocked with 1% bovine serum albumin for 2 hours at room temperature, and washed 5 times with PBST. 100 μL/well of hybridoma supernatant was added, incubated for 1 hour at room temperature, and then washed 5 times with PBST. 100 μL/well of HRP-labeled goat anti-mouse secondary antibody (Invitrogen, Cat #: 31430) was added, and incubated for 1 hour at room temperature after washing. 50 μL/well of 3,3',5,5'-tetramethylbenzidine (TMB) was then added to the plate, incubated at room temperature for 15 minutes, then the reaction was stopped and the results were read. Positive hybridomas were selected by ELISA screening, transferred to 24-well culture plate from 96-well culture plate for expanded culture, and the supernatant in the 24-well culture plate was re-screened after 5 days, and the re-screening was analyzed by flow cytometry (FACS).

2. Flow Cytometry Screening

Construction of lentiviral transfer plasmid encoding a CAR targeting CD19 and preparation of lentiviral vectors: 1) The chimeric gene encoding Strep-Tag II and scFv targeting CD19 was synthesized by gene synthesis method (Beijing Biomed Gene Technology Co., Ltd.). 2) Using the existing plasmid of a CAR targeting CD19 as a template (for the nucleotide sequence of a CAR targeting CD19, see SEQ ID NO: 13 in patent CN 105177031B), PCR was used to clone the nucleic acid fragment of the CAR molecule containing CD8α hinge region, CD8α transmembrane region, intracellular region of 4-IBB (corresponding to NP_001552.2), and intracellular region of CD3ζ (corresponding to NP_000725.1). 3) Using the chimeric gene obtained in step 1) and the nucleic acid fragment obtained in step 2) as templates, complete nucleic acid fragment encoding Strep-Tag II and a CAR targeting CD19 was cloned by PCR. 4) The complete nucleic acid fragment obtained in step 3) was inserted into lentiviral vector pLenti6.3/V5 (Thermo Fisher, Waltham, MA, USA) by the method of restriction enzyme digestion and ligation to obtain a lentiviral transfer plasmid bearing genes of Strep-Tag II and a CAR targeting to CD19. 5) The lentiviral packaging plasmids pLP/VSVG, pLP1/MDK, pLP2/RSK (Thermo Fisher, Waltham, MA, USA) and the transfer plasmids obtained in step 4) were transfected into HEK293T cells using Lipofectamine 3000 (Thermo Fisher, Waltham, MA, USA), the culture medium was collected after 48 hours, centrifuged at 300 g to remove cell debris, and centrifuged at 25,000 rpm for 3 hours with an ultracentrifuge. The precipitate was dissolved in 1 mL of physiological saline, to obtain the desired lentiviral vector.

Preparation of CAR-T cells containing a Strep-Tag II tag: T cells were isolated from peripheral blood mononuclear cells (Miao Tong (Shanghai) Biological Science & Technology Co., Utd., China) of healthy volunteers using CD3/CD28 Dynabeads (Thermo Fisher), the isolated T cells (the T cells at this time were linked with CD3/CD28 Dynabeads) were cultured in a fresh X-VIVO 15 culture system containing IL-2 (500 IU/mL) for 48 hours, and the above lentiviral vector was used to infect T cells. 24 hours after virus infection of cells, the cells were centrifuged to change the medium, and the culture was continued in the above-mentioned culture system. After 4 days of cell culture, all cells in the culture system were collected, the Dynabeads in the culture system were removed with a magnetic stand, T cells were centrifuged and counted, and CAR-T cell content was detected by a flow cytometer (NovoCyte 2060R, ACEA Biosciences, San Diego, CA, USA).

The above CAR-T cells containing a Strep-Tag II tag were collected, washed with DPBS and counted, and the cells were dispensed into EP tubes at approximately $3\times10^5$ cells per tube. After the supernatant was collected by centrifugation, 100 μL/well of hybridoma supernatant was added, and incubated at room temperature for 15 min. After washing twice, 5 μL of PE-labeled rat anti-mouse IgG (BD, Cat #: 550083) was added to each tube and incubated for 15 min at room temperature, and then cells were washed twice with DPBS and analyzed by flow cytometry FACS method.

3. Positive Subclones

Positive hybridoma clones were subcloned into 96-well plates by limiting dilution method, and positive monoclones were identified and selected by FACS screening method (same as above). RNA was extracted from the obtained monoclonal cells, and after reverse transcription into DNA, PCR was performed with primers that specifically bind to the heavy chain and light chain genes of the antibody, and the PCR products were sequenced.

Example 3

Sequencing

Positive monoclones were selected and total RNA was extracted by TRIZOL method. cDNA was generated by RT-PCR, and then the heavy and light chains were amplified by PCR respectively (RT-PCR kit was purchased from TransGen, Cat #: AE311-03, GXL high-fidelity DNA polymerase was used for PCR, purchased from TaKaRa, Cat #: R050A, see the product manual for specific operation). Then, the PCR product was cleaned with a cleaning kit (AXYGEN, Cat #: 155. See the product manual for specific operation), followed by sequencing, and the sequencing was handed over to Beijing Ruibiotech Co., Ltd. The amino acid sequences of the light chain variable region and the heavy chain variable region are as set forth in Tables 1 and 2, and the Sequence Listing. The screened antibody clone numbers are 8A882 and 8F8D1, respectively.

Example 4

Ascites Preparation and Antibody Purification

1. Ascites Preparation

Five Balb/c mice aged 6 to 8 weeks were ordered and injected with 1 mL of paraffin wax (purchased from Jiangxi Yipusheng Pharmaceutical Co., Ltd.) after one week of feeding, and each mouse was injected with $1\times10^6$ of monoclonal hybridoma cells in the next week. After one week, the mice were observed to have obvious abdominal distension, and the mice were punctured and aspirated every 48 hours. 3-4 mL of ascites was collected from each mouse, and a total of 20 mL of ascites was collected.

2. Antibody Purification

Figure 2:
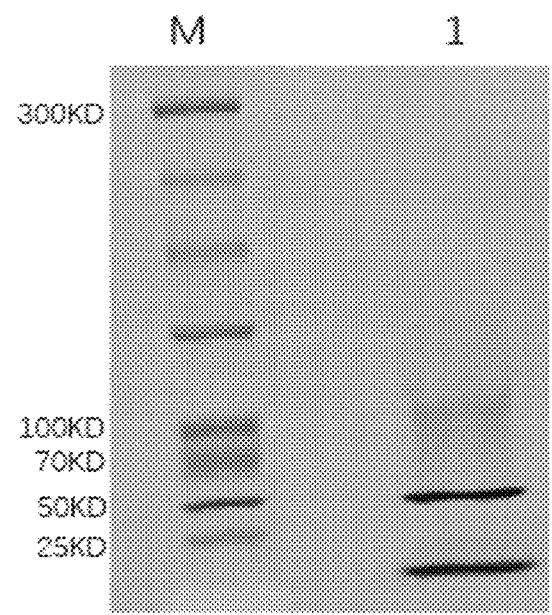
FIG. 2 shows the polyacrylamide gel electrophoresis pattern of antibody 8F8D1. Lane M is the molecular weight standard (within 300 KD); Lane 1 is the heavy chain (about 55 KD) and light chain (about 24 KD) of antibody 8F8D1.

The antibody was purified by affinity purification method, and the gravity column was equilibrated with Binding Buffer (pH 7.0) and washed with 2-5 times the column volume. The filtered ascites was passed through a column (ProteinA/G column, ordered from Thermo Fisher, Cat #: 89930); the column was washed with 5-10 times column volumes of Binding Buffer, and the target protein was eluted with 0.1 M glycine at pH 3.5, followed by adjustment to neutral with Tris-HCl at pH 9.0. Finally, BCA kit (Thermo; Cat #: 23227, see the product manual for specific operations) was used to determine the antibody concentration. The purity of the antibody was identified by SDS-PAGE, and FIG. 2 shows that the antibody has a high purity.

Example 5

Validation of Antibody and Detection of Affinity

1. Flow Cytometry Validation

Figure 3:
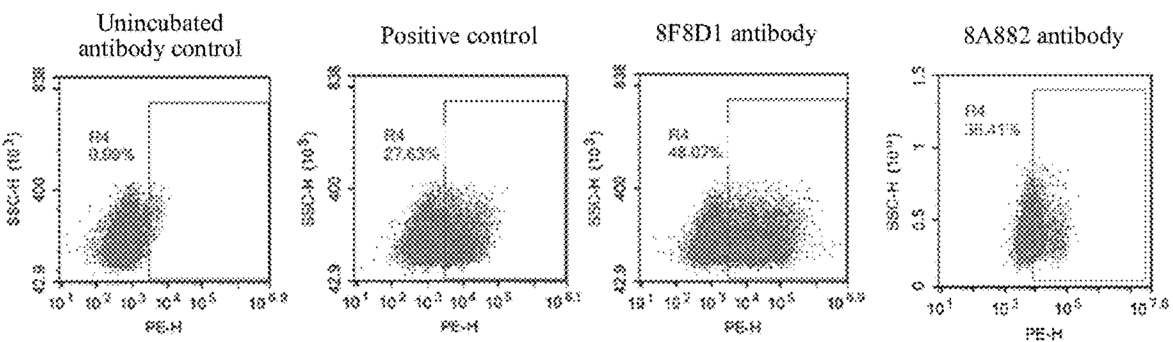
FIG. 3 shows the flow cytometry graph of antibodies 8F8D1 and 8A882.

The purified high-purity antibody was identified by FACS. The CAR-T cells containing a Strep-Tag II tag (manufactured by our company) prepared in Example 2.2 were collected, washed with FACS buffer and counted. The cells were dispensed into EP tubes at approximately $3\times10^5$ cells per tube. After centrifugation to remove the supernatant, 8A882 antibody or 8F8D1 antibody or positive control antibody was added at a final concentration of 1 μg/mL, and tubes were incubated at room temperature for 15 minutes. After washing twice, 5 μL of PE-labeled rat anti-mouse IgG was added to each tube, and incubated at room temperature for 15 minutes. The cells were then washed twice and FACS analysis was performed. The experimental results show that under the condition of the same amount of detection cells (CAR-T), after treatment with the 8F8D1 and 8A882 antibodies of the present invention, the expression rates of CAR-T cells containing a Strep-Tag II tag are 48.07% and 36.41%, respectively, which are much higher than the expression rate 27.63% of the positive control antibody treatment. The above results prove that the antibody of the present invention can specifically recognize the Strep-Tag II short peptide and the antibody of the present invention has a higher affinity for the Strep-Tag II short peptide than the commercial positive control antibody (FIG. 3). Negative control was Strep-Tag II tag antibody not added, but only negative control IgG was added, and positive control was commercial anti-Strep-Tag II tag antibody (Abcam; Cat #: ab184224).

2. Antibody Fluorescent Labeling

The antibodies of the present invention are labeled with two different fluorescences, FITC and PE, respectively, for the purpose of multi-site detection and analysis. Antibody fluorescent labeling was done by Beijing 4ABiotech Co., Ltd.

3. Fluorescence-Labeled Antibody Affinity Detection

The antibody affinity detection of the present invention adopts the dynamic equilibrium assay method (saturated concentration method). In the presence of a small amount of antigen, the antibody is subjected to gradient dilution to detect the concentration of the antigen-antibody complex. When the concentration of the antigen-antibody complex accounts for half of the total antigen concentration, the corresponding concentration value (EC50) of the antibody is the KD value of the antibody relative to the antigen.

Figure 4:
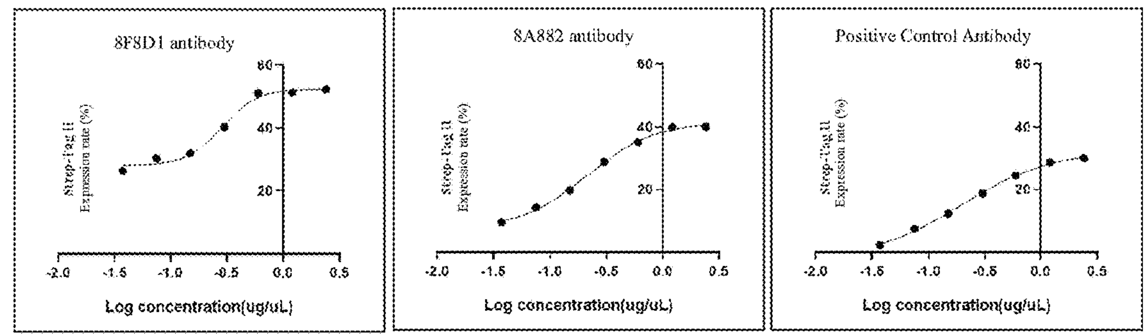
FIG. 4 shows the affinity test graph of antibodies 8F8D1 and 8A882.

CAR-T cells containing a Strep-Tag II tag were collected, washed with DPBS and counted. The cells were dispensed into several EP tubes at approximately $3\times10^5$ cells per tube. After centrifugation to remove the supernatant, 8A882 antibody or 8F8D1 antibody and a positive control antibody (commercial Strep-Tag II antibody, Abcam; Cat #: ab184224) diluted in serial gradient for 10 concentrations were added and incubated at room temperature for 15 minutes. After washing the cells twice with DPBS, PE-labeled rat anti-mouse IgG was added, and incubated at room temperature for 15 minutes. After washing the cells twice, FACS analysis and GraphPad Prism software were used to calculate the EC50 value. The EC50 values of 8A882 and 8F8D1 and the positive control antibody obtained by software analysis were 0.4 nM, 0.2 nM and 0.55 nM, respectively (FIG. 4). Compared with the positive control antibody, the two strain antibodies of the present invention have high affinity.

Example 6

Figure 5:
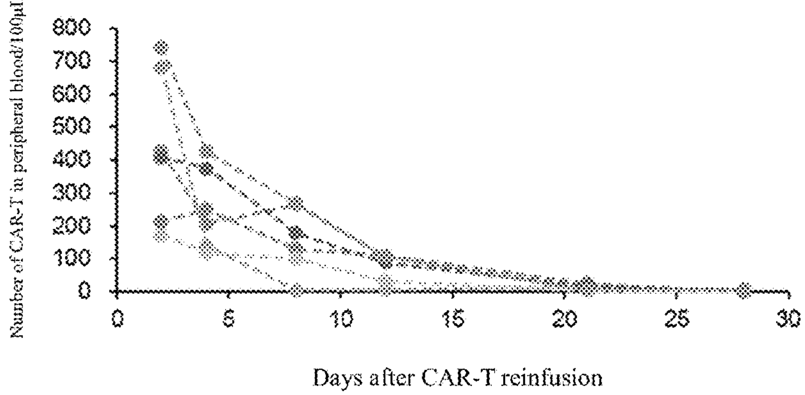
FIG. 5 shows the metabolism graph of CAR-T cells in mice monitored using antibody 8F8D1.

Detection of CAR-T Cells in Peripheral Blood of Tumor-Bearing Mice Using Antibodies A total of six 6-8 weeks old NCG mice (Jiangsu Gem-Pharmatech Co., Ltd, China) were injected $1.0\times10^6$ of Nalm-6-LAE cells (ATCC, USA) from the tail vein in each mouse, and 5 days later, the mice were analyzed by luciferase in vivo imaging (Lumina II small animal in vivo imaging system, PerkinElmer, USA) to confirm that the mouse leukemia model was successfully prepared, then each mouse was injected with CD19 CAR-T cells from the tail vein (prepared by our company with reference to the method in Example 2.2, $2\times10^6$ cells per mice). 100 μL peripheral blood was collected from the orbit of mice on days 2, 4, 8, 12, 21, and 28 after CAR-T cell injection for CAR-T detection. Specifically, the peripheral blood was divided into 2 aliquots of 50 μL each, and 3 μL of PE-labeled 8F8D1 antibody was added to each aliquot, mixed and incubated at room temperature and protected from light for 20 min; hemolysate was added to the samples, incubated at room temperature and protected from light for 15 min, washed twice with DPBS, and then resuspended with 100 μL of DPBS respectively, and the CAR-T ratio was analyzed by FACS and numbers of CAR-T cells per 100 μL of peripheral blood peripheral blood were calculated, and the metabolic profiles of CAR-T in each mouse were plotted (FIG. 5).

The data shows that the distribution of CAR-T cells in mice can be effectively detected using PE-labeled 8F8D1 antibody.

The invention claimed is:

1. An isolated antibody that specifically binds to a Strep-Tag II tag, comprising a heavy chain variable region (VH) and a light chain variable region (VL), wherein the VH comprises: a VH-CDR1 comprising SEQ ID NO: 1, a VH-CDR2 comprising SEQ ID NO: 2, a VH-CDR 3 comprising SEQ ID NO: 3 or SEQ ID NO: 4; and the VL comprises: a VL-CDR1 comprising SEQ ID NO: 5 or SEQ ID NO: 6, a VL-CDR2 comprising SEQ ID NO: 7 or SEQ ID NO: 8, a VL-CDR3 comprising SEQ ID NO: 9 or SEQ ID NO: 10.

2. The isolated antibody of claim 1, wherein the VH comprises: a VH-CDR1 comprising SEQ ID NO: 1, a VH-CDR2 comprising SEQ ID NO: 2, a VH-CDR3 comprising SEQ ID NO: 3; and the VL comprises: a VL-CDR1 comprising SEQ ID NO: 5, a VL-CDR2 comprising SEQ ID NO: 7, a VL-CDR3 comprising SEQ ID NO: 9; or the VH comprises: a VH-CDR1 comprising SEQ ID NO: 1, a VH-CDR2 comprising SEQ ID NO: 2, a VH-CDR3 comprising SEQ ID NO: 4; and the VL comprises: a VL-CDR1 comprising SEQ ID NO: 6, a VL-CDR2 comprising SEQ ID NO: 8, a VL-CDR3 comprising SEQ ID NO: 10.

3. The isolated antibody of claim 1, wherein the VH comprises the amino acid sequence of SEQ ID NO: 23 or 24, or comprises an amino acid sequence with at least 85% identity thereto; and the VL comprises the amino acid sequence of SEQ ID NO: 25 or 26, or comprises an amino acid sequence with at least 85% identity thereto.

4. The isolated antibody of claim 1, wherein the VH comprises one or more framework region(s), each of the framework regions comprises an amino acid sequence, the amino acid sequence is the sequence as set forth in SEQ ID NOs: 11, 12, 13, 14, 15 and 16, or an amino acid sequence with at least 90% identity thereto;

the VL comprises one or more framework region(s), each of the framework regions comprises an amino acid sequence, the amino acid sequence is the sequence as set forth in SEQ ID NOs: 17, 18, 19, 20, 21 and 22, or an amino acid sequence with at least 90% identity thereto.

5. The isolated antibody of claim 1, wherein the VH comprises the amino acid sequence of SEQ ID NO: 23, or an amino acid sequence with at least 85% identity thereto, and the VL comprises the amino acid sequence of SEQ ID NO: 25, or an amino acid sequence with at least 85% identity thereto; or the VH comprises the amino acid sequence of SEQ ID NO: 24, or an amino acid sequence with at least 85% identity thereto, and the VL comprises the amino acid sequence of SEQ ID NO: 26, or an amino acid sequence with at least 85% identity thereto.

6. The isolated antibody of claim 1, wherein the antibody comprises the amino acid sequence of SEQ ID NO: 27 or 29, or an amino acid sequence with at least 85% identity thereto; and the antibody comprises the amino acid sequence of SEQ ID NO: 28 or 30, or an amino acid sequence with at least 85% identity thereto.

7. The isolated antibody of claim 1, wherein the antibody comprises the amino acid sequence of SEQ ID NO: 27, or an amino acid with at least 85% identity thereto; and the antibody comprises the amino acid sequence of SEQ ID NO: 28, or an amino acid sequence with at least 85% identity thereto; or the antibody comprises the amino acid sequence of SEQ ID NO: 29, or an amino acid sequence with at least 85% identity thereto, and the antibody comprises SEQ ID NO: 30, or an amino acid sequence with at least 85% identity thereto.

8. An isolated nucleic acid encoding the isolated antibody of claim 1.

9. A cloning or expression vector comprising the isolated nucleic acid of claim 8.

10. A host cell comprising the isolated nucleic acid of claim 8.

11. An antibody conjugate comprising the isolated antibody of claim 1 linked to a label, wherein the label is selected from fluorescent labels, enzyme substrate labels, radioactive isotopes, digoxigenin, biotin or avidin, DNA molecules or gold for detection.

12. A composition or kit comprising the antibody conjugate of claim 11, and one or more pharmaceutically acceptable excipient(s), diluent(s) or carrier(s).

13. The antibody conjugate of claim 11, wherein the fluorescent label is selected from fluorescein, rhodamine, dansyl, phycoerythrin or Texas red; and/or wherein the enzyme substrate label is selected from horseradish peroxidase, alkaline phosphatase, glucoamylase, lysozyme, saccharide oxidase or β-D-galactosidase; and/or wherein the radioactive isotope is selected from $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, $^{32}P$; and/or wherein the label is selected from a luminescent label or a chromophore.

14. A composition or kit comprising the isolated antibody of claim 1, and one or more pharmaceutically acceptable excipient(s), diluent(s) or carrier(s).

15. A method of detecting a fusion polypeptide containing a Strep-Tag II tag in a sample, comprising:

(i) contacting the sample containing the fusion polypeptide with the isolated antibody of claim 1 in vitro, under conditions that allow the interaction between the isolated antibody and the fusion polypeptide, and (ii) detecting formation of complex between the isolated antibody and the sample.

16. The method of claim 15, wherein the sample is a biological sample comprising at least one of blood, urine, saliva, lymph, cerebrospinal fluid, bone marrow, tissues, organs, and cells.

17. The method of claim 16, wherein the blood comprises at least one of serum, plasma and whole blood; and/or wherein the sample contains chimeric antigen receptor cells or engineered cell receptor cells.

18. The method of claim 15, wherein the method of detecting the complex comprises at least one of flow cytometry, Western blot, immunohistochemistry, and immunofluorescence.

19. A method of purifying a fusion polypeptide containing a Strep-Tag II tag in a sample, comprising (i) contacting the sample with the isolated antibody of claim 1 in vitro, under conditions that allow the interaction between the isolated antibody and the polypeptide, and (ii) purifying the complex formed between the isolated antibody and the sample.

20. The method of claim 19, wherein the method of purifying comprises affinity chromatography and immunoprecipitation.

* * * * *

SEQUENCE LISTING

```
<160> NUMBER OF SEQ ID NOS: 30

<210> SEQ ID NO 1
<211> LENGTH: 10
<212> TYPE: PRT
<213> ORGANISM: Artificial Sequence
<220> FEATURE:
<223> OTHER INFORMATION: VH-CDR1

<400> SEQUENCE: 1

Gly Tyr Thr Phe Thr Asp Tyr Tyr Met Lys
1               5                   10


<210> SEQ ID NO 2
<211> LENGTH: 17
<212> TYPE: PRT
<213> ORGANISM: Artificial Sequence
<220> FEATURE:
<223> OTHER INFORMATION: VH-CDR2

<400> SEQUENCE: 2

Asp Ile Asn Pro Asn Asn Gly Asp Thr Phe Tyr Asn Gln Lys Phe Lys
1               5                   10                  15

Gly


<210> SEQ ID NO 3
<211> LENGTH: 11
<212> TYPE: PRT
<213> ORGANISM: Artificial Sequence
<220> FEATURE:
<223> OTHER INFORMATION: VH-CDR3

<400> SEQUENCE: 3

Tyr Tyr Gly Asn Ser Ser Pro Trp Phe Ala Tyr
1               5                   10


<210> SEQ ID NO 4
<211> LENGTH: 11
<212> TYPE: PRT
<213> ORGANISM: Artificial Sequence
<220> FEATURE:
<223> OTHER INFORMATION: VH-CDR3

<400> SEQUENCE: 4

Tyr Tyr Gly Arg Ser Ser Pro Trp Phe Pro Tyr
1               5                   10
```

<210> SEQ ID NO 5
<211> LENGTH: 15
<212> TYPE: PRT
<213> ORGANISM: Artificial Sequence
<220> FEATURE:
<223> OTHER INFORMATION: VL-CDR1

<400> SEQUENCE: 5

```
Lys Ala Ser Gln Ser Val Asp Tyr Asp Gly Asp Ser Tyr Met Asn
1               5                   10                  15
```

<210> SEQ ID NO 6
<211> LENGTH: 15
<212> TYPE: PRT
<213> ORGANISM: Artificial Sequence
<220> FEATURE:
<223> OTHER INFORMATION: VL-CDR1

<400> SEQUENCE: 6

```
Lys Ala Ser Gln Ser Val Asp Asn Ser Gly Asp Ser Tyr Met Asn
1               5                   10                  15
```

<210> SEQ ID NO 7
<211> LENGTH: 7
<212> TYPE: PRT
<213> ORGANISM: Artificial Sequence
<220> FEATURE:
<223> OTHER INFORMATION: VL-CDR2

<400> SEQUENCE: 7

```
Ala Ala Ser Asn Leu Gln Ser
1               5
```

<210> SEQ ID NO 8
<211> LENGTH: 7
<212> TYPE: PRT
<213> ORGANISM: Artificial Sequence
<220> FEATURE:
<223> OTHER INFORMATION: VL-CDR2

<400> SEQUENCE: 8

```
Ala Ala Ser Asn Leu Glu Ser
1               5
```

<210> SEQ ID NO 9
<211> LENGTH: 9
<212> TYPE: PRT
<213> ORGANISM: Artificial Sequence
<220> FEATURE:
<223> OTHER INFORMATION: VL-CDR3

<400> SEQUENCE: 9

```
Gln Gln Ile Thr Glu Asp Pro Trp Thr
1               5
```

<210> SEQ ID NO 10
<211> LENGTH: 9
<212> TYPE: PRT
<213> ORGANISM: Artificial Sequence
<220> FEATURE:
<223> OTHER INFORMATION: VL-CDR3

<400> SEQUENCE: 10

```
Gln Gln Ile Asn Glu Asp Pro Trp Thr
1               5
```

<210> SEQ ID NO 11
<211> LENGTH: 25
<212> TYPE: PRT
<213> ORGANISM: Artificial Sequence
<220> FEATURE:
<223> OTHER INFORMATION: VH-FWR1

<400> SEQUENCE: 11

Glu Val Gln Leu Gln Gln Ser Gly Pro Glu Leu Val Lys Pro Gly Ala
1 5 10 15

Ser Val Lys Met Ser Cys Lys Ala Ser
20 25

<210> SEQ ID NO 12
<211> LENGTH: 14
<212> TYPE: PRT
<213> ORGANISM: Artificial Sequence
<220> FEATURE:
<223> OTHER INFORMATION: VH-FWR2

<400> SEQUENCE: 12

Trp Val Lys Gln Ser His Gly Lys Ser Leu Glu Trp Ile Gly
1 5 10

<210> SEQ ID NO 13
<211> LENGTH: 14
<212> TYPE: PRT
<213> ORGANISM: Artificial Sequence
<220> FEATURE:
<223> OTHER INFORMATION: VH-FWR2

<400> SEQUENCE: 13

Trp Val Lys Gln Ser His Gly Lys Arg Leu Glu Trp Ile Gly
1 5 10

<210> SEQ ID NO 14
<211> LENGTH: 32
<212> TYPE: PRT
<213> ORGANISM: Artificial Sequence
<220> FEATURE:
<223> OTHER INFORMATION: VH-FWR3

<400> SEQUENCE: 14

Lys Ala Thr Leu Thr Val Asp Lys Ser Ser Ser Ser Ala Tyr Met Gln
1 5 10 15

Leu Asn Ser Leu Thr Ser Glu Asp Ser Ala Val Tyr Tyr Cys Ala Arg
20 25 30

<210> SEQ ID NO 15
<211> LENGTH: 32
<212> TYPE: PRT
<213> ORGANISM: Artificial Sequence
<220> FEATURE:
<223> OTHER INFORMATION: VH-FWR3

<400> SEQUENCE: 15

Lys Ala Thr Leu Thr Val Asp Lys Ser Ser Ser Thr Ala Tyr Met Gln
1 5 10 15

Leu Asn Ser Leu Thr Ser Glu Asp Ser Ala Val Tyr Tyr Cys Ala Arg
20 25 30

<210> SEQ ID NO 16
<211> LENGTH: 11
<212> TYPE: PRT
<213> ORGANISM: Artificial Sequence
<220> FEATURE:

```
<223> OTHER INFORMATION: VH-FWR4

<400> SEQUENCE: 16

Trp Gly Gln Gly Thr Leu Val Thr Val Ser Ala
1               5                   10


<210> SEQ ID NO 17
<211> LENGTH: 23
<212> TYPE: PRT
<213> ORGANISM: Artificial Sequence
<220> FEATURE:
<223> OTHER INFORMATION: VL-FWR1

<400> SEQUENCE: 17

Asp Ile Val Leu Thr Gln Ser Pro Ala Ser Leu Ala Val Ser Leu Gly
1               5                   10                  15

Gln Arg Ala Thr Ile Ser Cys
            20


<210> SEQ ID NO 18
<211> LENGTH: 23
<212> TYPE: PRT
<213> ORGANISM: Artificial Sequence
<220> FEATURE:
<223> OTHER INFORMATION: VL-FWR1

<400> SEQUENCE: 18

Asp Ile Val Leu Thr Gln Ser Pro Ala Ser Leu Gly Val Ser Leu Gly
1               5                   10                  15

Gln Arg Ala Thr Ile Ser Cys
            20


<210> SEQ ID NO 19
<211> LENGTH: 15
<212> TYPE: PRT
<213> ORGANISM: Artificial Sequence
<220> FEATURE:
<223> OTHER INFORMATION: VL-FWR2

<400> SEQUENCE: 19

Trp Tyr Gln Gln Lys Pro Gly Gln Pro Pro Lys Leu Leu Ile Tyr
1               5                   10                  15


<210> SEQ ID NO 20
<211> LENGTH: 32
<212> TYPE: PRT
<213> ORGANISM: Artificial Sequence
<220> FEATURE:
<223> OTHER INFORMATION: VL-FWR3

<400> SEQUENCE: 20

Gly Ile Pro Ala Arg Phe Ser Gly Ser Gly Ser Gly Thr Asp Phe Thr
1               5                   10                  15

Leu Asn Ile His Pro Val Glu Glu Glu Asp Thr Ala Thr Tyr Tyr Cys
            20                  25                  30


<210> SEQ ID NO 21
<211> LENGTH: 32
<212> TYPE: PRT
<213> ORGANISM: Artificial Sequence
<220> FEATURE:
<223> OTHER INFORMATION: VL-FWR3

<400> SEQUENCE: 21

Gly Ile Pro Ala Arg Phe Ser Gly Ser Gly Ser Gly Thr Asp Phe Thr
```

-continued

```
1               5                   10                  15

Leu Asn Ile His Pro Val Glu Glu Glu Asp Ala Ala Thr Tyr Tyr Cys
            20                  25                  30


<210> SEQ ID NO 22
<211> LENGTH: 10
<212> TYPE: PRT
<213> ORGANISM: Artificial Sequence
<220> FEATURE:
<223> OTHER INFORMATION: VL-FWR4

<400> SEQUENCE: 22

Phe Gly Gly Arg Thr Lys Leu Glu Ile Lys
1               5                   10


<210> SEQ ID NO 23
<211> LENGTH: 120
<212> TYPE: PRT
<213> ORGANISM: Artificial Sequence
<220> FEATURE:
<223> OTHER INFORMATION: Heavy Chain Variable Region

<400> SEQUENCE: 23

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Asn Gly Asp Thr Phe Tyr Asn Gln Lys Phe
    50                  55                  60

Lys Gly Lys Ala Thr Leu Thr Val Asp Lys Ser Ser Ser Ser Ala Tyr
65                  70                  75                  80

Met Gln Leu Asn Ser Leu Thr Ser Glu Asp Ser Ala Val Tyr Tyr Cys
                85                  90                  95

Ala Arg Tyr Tyr Gly Asn Ser Ser Pro Trp Phe Ala Tyr Trp Gly Gln
            100                 105                 110

Gly Thr Leu Val Thr Val Ser Ala
        115                 120


<210> SEQ ID NO 24
<211> LENGTH: 120
<212> TYPE: PRT
<213> ORGANISM: Artificial Sequence
<220> FEATURE:
<223> OTHER INFORMATION: Heavy Chain Variable Region

<400> SEQUENCE: 24

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Arg Leu Glu Trp Ile
        35                  40                  45

Gly Asp Ile Asn Pro Asn Asn Gly Asp Thr Phe Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95
```

```
Ala Arg Tyr Tyr Gly Arg Ser Ser Pro Trp Phe Pro Tyr Trp Gly Gln
            100                 105                 110

Gly Thr Leu Val Thr Val Ser Ala
        115                 120


<210> SEQ ID NO 25
<211> LENGTH: 111
<212> TYPE: PRT
<213> ORGANISM: Artificial Sequence
<220> FEATURE:
<223> OTHER INFORMATION: Light Chain Variable Region

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Gln Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ile Thr
                85                  90                  95

Glu Asp Pro Trp Thr Phe Gly Gly Arg Thr Lys Leu Glu Ile Lys
            100                 105                 110


<210> SEQ ID NO 26
<211> LENGTH: 111
<212> TYPE: PRT
<213> ORGANISM: Artificial Sequence
<220> FEATURE:
<223> OTHER INFORMATION: Light Chain Variable Region

<400> SEQUENCE: 26

Asp Ile Val Leu Thr Gln Ser Pro Ala Ser Leu Gly Val Ser Leu Gly
1               5                   10                  15

Gln Arg Ala Thr Ile Ser Cys Lys Ala Ser Gln Ser Val Asp Asn Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ile Asn
                85                  90                  95

Glu Asp Pro Trp Thr Phe Gly Gly Arg Thr Lys Leu Glu Ile Lys
            100                 105                 110


<210> SEQ ID NO 27
<211> LENGTH: 444
<212> TYPE: PRT
<213> ORGANISM: Artificial Sequence
<220> FEATURE:
<223> OTHER INFORMATION: Heavy Chain

<400> SEQUENCE: 27
```

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Asn Gly Asp Thr Phe Tyr Asn Gln Lys Phe
    50                  55                  60

Lys Gly Lys Ala Thr Leu Thr Val Asp Lys Ser Ser Ser Ser Ala Tyr
65                  70                  75                  80

Met Gln Leu Asn Ser Leu Thr Ser Glu Asp Ser Ala Val Tyr Tyr Cys
                85                  90                  95

Ala Arg Tyr Tyr Gly Asn Ser Ser Pro Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Pro Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
```

```
            420                 425                 430

His Thr Glu Lys Ser Leu Ser His Ser Pro Gly Lys
        435                 440


<210> SEQ ID NO 28
<211> LENGTH: 218
<212> TYPE: PRT
<213> ORGANISM: Artificial Sequence
<220> FEATURE:
<223> OTHER INFORMATION: Light Chain

<400> SEQUENCE: 28

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Gln Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ile Thr
                85                  90                  95

Glu Asp Pro Trp Thr Phe Gly Gly Arg Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 29
<211> LENGTH: 444
<212> TYPE: PRT
<213> ORGANISM: Artificial Sequence
<220> FEATURE:
<223> OTHER INFORMATION: Heavy Chain

<400> SEQUENCE: 29

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Arg Leu Glu Trp Ile
        35                  40                  45

Gly Asp Ile Asn Pro Asn Asn Gly Asp Thr Phe Tyr Asn Gln Lys Phe
    50                  55                  60
```

-continued

```
Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Tyr Tyr Gly Arg Ser Ser Pro Trp Phe Pro Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Pro Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440
```

```
<210> SEQ ID NO 30
<211> LENGTH: 218
<212> TYPE: PRT
<213> ORGANISM: Artificial Sequence
<220> FEATURE:
<223> OTHER INFORMATION: Light Chain
```

```
<400> SEQUENCE: 30

Asp Ile Val Leu Thr Gln Ser Pro Ala Ser Leu Gly Val Ser Leu Gly
1               5                   10                  15

Gln Arg Ala Thr Ile Ser Cys Lys Ala Ser Gln Ser Val Asp Asn Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ile Asn
                85                  90                  95

Glu Asp Pro Trp Thr Phe Gly Gly Arg Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```